United States Patent [19]

Arimatsu

[11] 4,450,713

[45] May 29, 1984

[54] METHOD FOR MEASURING HARDNESS OF RUBBER AND PLASTICS AND A HARDNESS TESTER FOR USE THEREIN

[75] Inventor: Toshio Arimatsu, Akashi, Japan

[73] Assignee: Sumitomo Rubber Industries, Ltd., Kobe, Japan

[21] Appl. No.: 389,156

[22] Filed: Jun. 16, 1982

[30] Foreign Application Priority Data

Jun. 24, 1981 [JP] Japan .................................. 56-99436

[51] Int. Cl.$^3$ .............................................. G01N 3/42
[52] U.S. Cl. ........................................ 73/81; 374/142
[58] Field of Search .................. 73/78, 79, 81, 82, 83, 73/85; 374/142

[56] References Cited

U.S. PATENT DOCUMENTS

| | | | |
|---|---|---|---|
| 3,576,127 | 4/1971 | Weitzel | 73/79 |
| 4,111,039 | 9/1978 | Yamawaki et al. | 73/82 |
| 4,331,026 | 5/1982 | Howard | 73/81 |
| 4,383,450 | 5/1983 | Pringiers | 73/81 |

*Primary Examiner*—S. Clement Swisher
*Attorney, Agent, or Firm*—Wenderoth, Lind & Ponack

[57] ABSTRACT

The invention relates to a method for measuring the hardness of rubber, plastics, etc. and a hardness tester for use therein, characterized in that a feeler of the hardness tester is brought into contact with the surface of a test material, the amount of displacement of the feeler is converted into electric signals, the variation of hardness from the maximum value directly after the testing to the stabilized value after the lapse of a preset space of time is measured, and the temperature of the test material is taken synchronously with the hardness testing. The hardness tester comprises a hardness sensor for detecting the displacement of the feeler of the hardness tester in terms of a variation in voltage, an evaluation unit for converting the variation in voltage into a digital signal for hardness, a maximum value detecting circuit connected with the evaluation unit, a time presetting switch part, a timer, and a display part for making a digital display of the variation from the maximum value of hardness to the stabilized value of hardness after the lapse of a preset space of time, thereby enabling an operator to detect with precision the variation of hardness of the test material.

3 Claims, 10 Drawing Figures

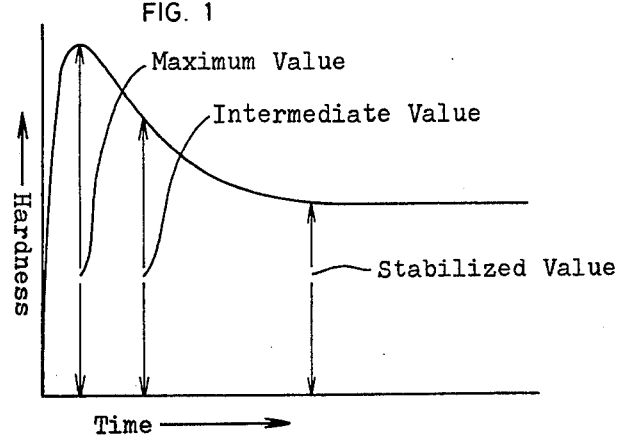
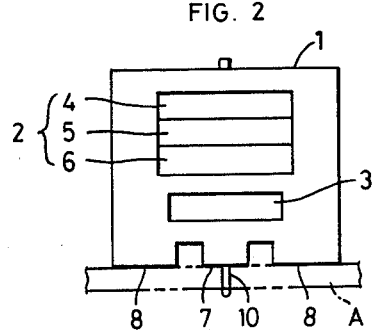
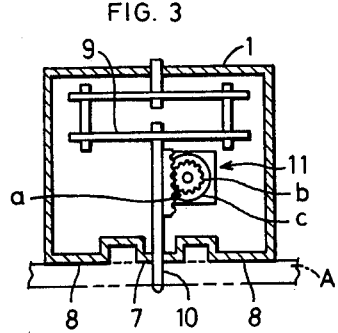
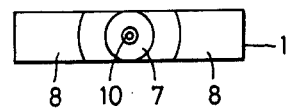

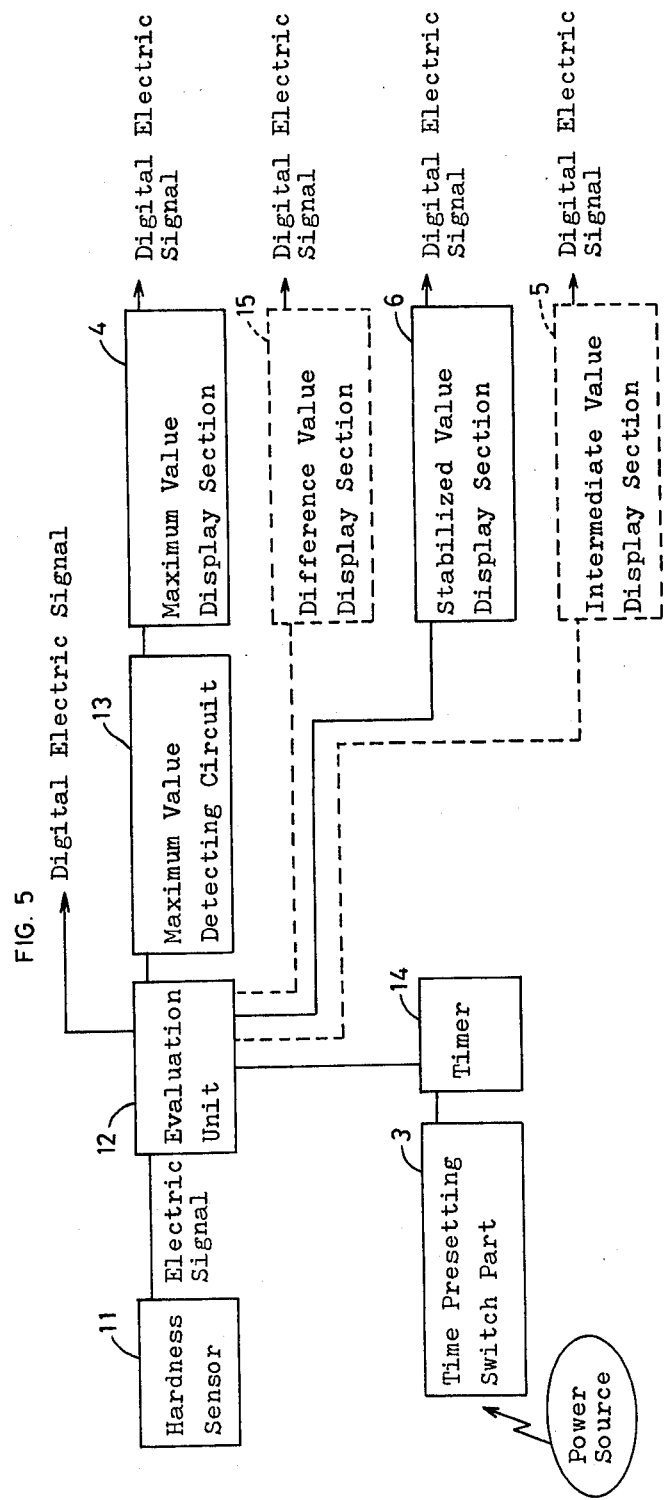

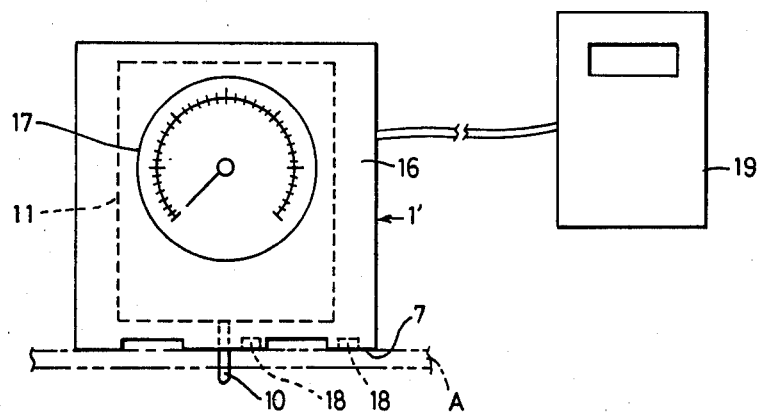
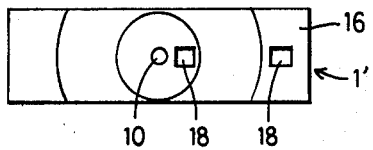
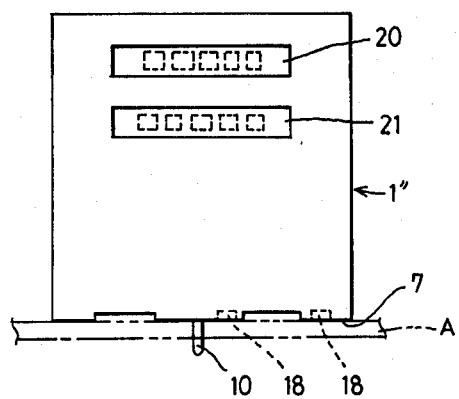

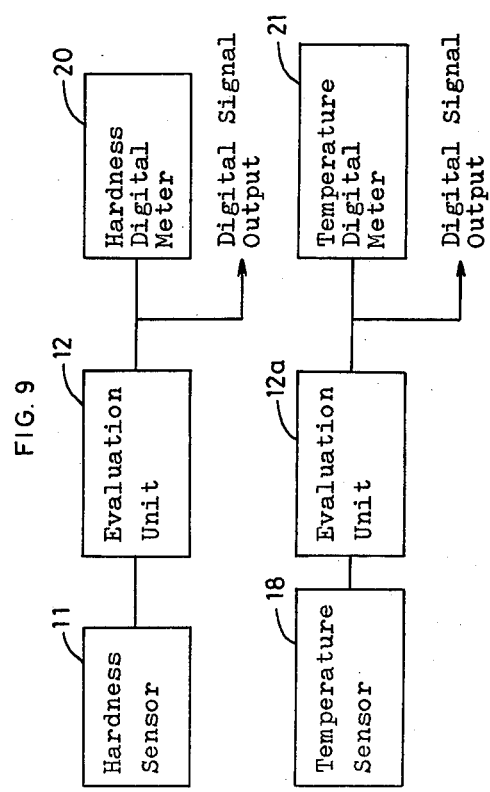

METHOD FOR MEASURING HARDNESS OF RUBBER AND PLASTICS AND A HARDNESS TESTER FOR USE THEREIN

BACKGROUND OF THE INVENTION

1. Field of the Invention

The invention relates to a method for measuring the hardness of rubber, plastics, etc. and a hardness tester for use therein.

2. Description of the Prior Art

The hardness of rubber, plastics, etc. is frequently tested as one of the important properties thereof. Conventionally, such hardness was usually tested by the dial gauge system wherein a feeler of the hardness tester was pressed against the test material, the displacement of the feeler being converted into an amount of rotation, for example, with the aid of a spring unit and rack-and-pinion unit, thereby enabling the operator to measure the hardness by reading graduations on the dial plate.

The inventors have found that the value of said property (hardness) of rubber, plastics, etc. is highest directly after the feeler of the hardness tester is pressed against the test material, the hardness being gradually reduced until the value is substantially stabilized after the lapse of a preset space of time. It has also been found that the variation (reduction) of hardness exerts an important influence on the quality of the test material, for example, the gripping property in case of tires. Since the variation of hardness is instantaneous, it has been difficult for the conventional hardness tester to take an accurate measurement thereof.

In the test of hardness of rubber, plastics, etc. by a hardness tester, the hardness considerably varies in practice according to the temperature of the test material. Thus, unless the temperature of the test material is specified each time its hardness is tested, the data are sometimes useless due to their wide variation. Conventionally, however, the temperature data were practically ignored because of the trouble of taking the temperature of the test material on each occasion of hardness testing.

SUMMARY OF THE INVENTION

In view of the above-described difficulties, the invention has for an object to provide a method for exactly measuring, displaying or recording said instantaneous variation of hardness synchronously with the corresponding temperature data, and a hardness tester for use therein.

BRIEF DESCRIPTION OF THE DRAWINGS

Some of the embodiments of the invention will hereinunder be described in detail in reference to the accompanying drawings, of which:

FIG. 1 is a curve showing the variation of hardness;

FIG. 2 is an elevational view showing an embodiment of the hardness tester according to the invention;

FIG. 3 is a longitudinal sectional elevation of the same;

FIG. 4 is a bottom view of the same;

FIG. 5 is a block diagram for measuring the variation of hardness;

FIG. 6 is an elevational view showing another embodiment of the hardness tester according to the invention;

FIG. 7 is a bottom view of the same;

FIG. 8 is an elevational view of a hardness tester according to a still further embodiment of the invention;

FIG. 9 is a block diagram showing evaluation circuits and display circuits of a hardness sensor and a temperature sensor, respectively.

DETAILED DESCRIPTION OF THE PREFERRED EMBODIMENTS

Figure 10:
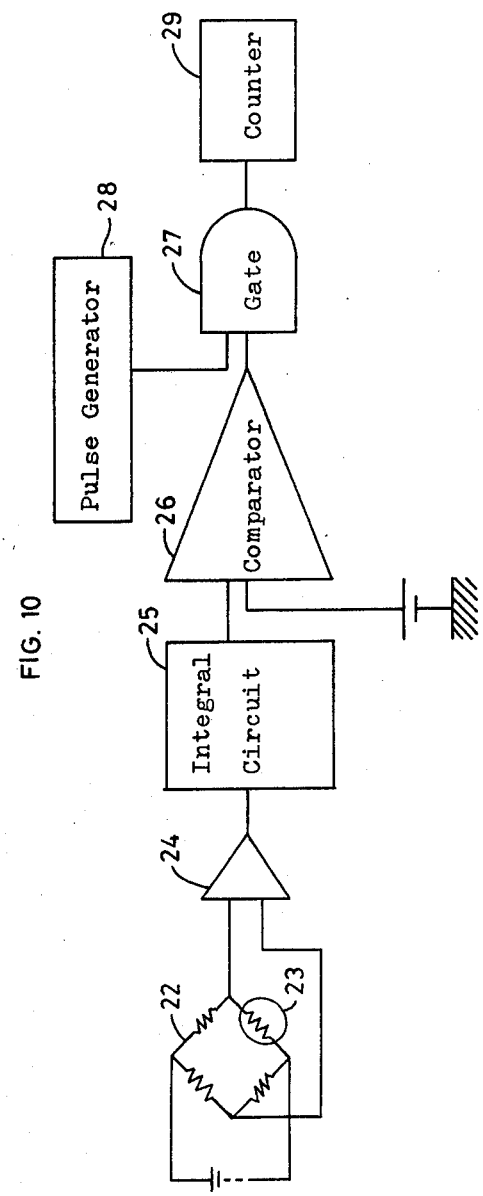
FIG. 10 is a block diagram showing a temperature sensor and an evaluation circuit, respectively.

As shown in FIGS. 2 to 5, the hardness tester 1 is provided on the front with a display part 2 and a time presetting switch part 3. The display part 2 comprises a maximum value display section 4, an intermediate value display section 5, a stabilized value display section 6 and a difference value display section 15 (FIG. 5 only), each for making a digital display of hardness by means of the known liquid crystals or the like.

The division of the display part 2 is optional; for example, it may be limited to a maximum value display section 4 and a stabilized value display section 6 only.

The under surface of the hardness tester is formed with fixed supports 7,8,8 to be brought into contact with test material (A) as is commonly known. A feeler 10 is connected at one end thereof to an inside plate spring unit 9 projecting at the other end thereof beyond the fixed support 7 in the center.

The plate spring unit 9 is adapted to have a fixed interrelation between stress and displacement regulated by the Japanese Industrial Standards. The feeler 10 is integrated with a rack (a) meshing with a pinion (b), a rheostat (c) being coupled with the shaft of the pinion (b), thereby enabling the operator to convert the amount of displacement of the feeler 10 into rotation of the pinion (b) and to measure it as a variation of voltage (electric amount) through the rheostat (c). A differential transformer, a rotary encoder and the like may also be utilized.

The electric signal from the aforedescribed hardness sensor 11 (FIGS. 3, 5 and 6) is provided as an input to the evaluation unit 12 (FIGS. 5 and 9). The evaluation unit 12 outputs the electric signal from the hardness sensor 11 as a signal coinciding with the digital amount of hardness as commonly known. Said evaluation unit 12 comprises a counter circuit, an A/D converter, a logic circuit or a microcomputer, the output thereof digitally displaying the maximum value of hardness in the maximum value display section 4 through the maximum value detecting circuit 13 (FIG. 5 only), while digitally displaying the stabilized value of hardness in the stabilized value display section 6, for example, after the lapse of 1 second in collaboration with the timer 14 (FIG. 5 only) preset in the time presetting switch part 3.

As shown in FIG. 5, the difference value display section 15 may be provided in place of or in addition to the stabilized value display section 6 so that the difference between the maximum value and the stabilized value is digitally displayed therein.

Alternatively, an intermediate value display section 5 may be provided in addition to the maximum value display section 4 and the stabilized value display section 6 so that the instantaneous variation of hardness, for example, in terms of a millisecond, is digitally displayed therein, thereby enabling the operator to detect the hardness when the value is substantially stabilized ultimately.

It may be so arranged that the digital signals of the maximum value, intermediate value, stabilized value and difference value can be taken out respectively, when necessary. Such digital signals can be recorded by providing them to a printer unit (not shown) or can be subjected to data processing by providing them to a computer and the like.

The digital signals from the evaluation unit 12, in particular, can be subjected to data processing including the maximum value detection and the like by providing said signals to a computer and the like.

The space of time to be preset in the time presetting switch part 3 depends on the kind of test material. Therefore, it is to be determined from experience.

Referring to FIGS. 6 and 7, the hardness tester 1' is provided with a tester body 16 in the shape of a flat square box having a thin thickness compared with the transverse width and height thereof, a flat fixed support part 7 to be brought into contact with the test material (A) being formed on the bottom part of the tester body 16, a hardness sensor 11 being incorporated in the interior of said tester body 16.

The hardness sensor 11 is provided with a feeler 10 adapted to project normally beyond the fixed support part 7 and retract when brought into contact with test material (A). The hardness measured by the hardness sensor 11 through its feeler 10 is displayed on a dial plate 17 provided on the front of the tester body 16.

On the fixed support part 7 of the tester body 16 there is provided a temperature sensor 18 adjacent the feeler 10 or transversely at one end of said fixed support part 7.

The temperature sensor 18 comprises a thermistor, a thermocouple, a platinum resistor and a semiconductor sensor. The temperature sensor 18 is buried in the fixed support part 7 so that the sensor part is flush with the fixed support part 7 thereby enabling it to be brought into face-to-face contact with the test material (A) when the latter is in contact with the surface.

The hardness tester 1' is connected with a temperature display unit 19 so that said unit 19 can display the temperature data provided by the temperature sensor 18.

Thus, when hardness of test material (A) is tested by the afore-described hardness tester 1', the hardness data detected by the hardness sensor 11 are displayed by the indicator on dial plate 17, while the temperature data detected by the temperature sensor 18 are displayed by the temperature display unit 19.

In said hardness tester 1', the hardness data and the temperature data are independently displayed on the dial plate 17 and the display unit 19 respectively.

Alternatively, the hardness tester 1'' shown in FIG. 8 is adapted to display synchronously the hardness data and the temperature data by digital meters 20, 21 consisting of light emitting diodes, liquid crystals, etc. provided on the front of the tester body.

In this case, as shown in FIG. 9, the outputs from the hardness sensor 11 and the temperature sensor 18 are subjected to data processing through the evaluation units 12 and 12a and are displayed by digital meters 20, 21 respectively.

As shown in FIG. 10, the temperature sensor 18 (FIG. 9) comprises a thermistor 23 incorporated in a bridge circuit 22, the evaluation unit 12a (FIG. 9) transmitting the output signals of the bridge circuit 22 through an integral circuit 25 by amplifying it by means of a DC amplifier 24, said signals being compared with the basic signals by a comparator 26, the opening time of the gate 27 being determined by the output signal of said comparator 26 in conformity with the measured temperature, pulse signals being taken out of the pulse generator 28, said pulse signals being counted by a counter 29, the count of said counter 29 being adapted to be displayed by a digital meter 21. It may be so arranged that digital signal outputs from the evaluation units 12, 12a are independently provided to a computer for data processing or to a printer for recording.

This commonly known circuit structure suffices also in a case where the temperature sensor 18 is a semiconductor sensor.

The hardness tester according to the invention has an advantage in that not only the reduction of hardness constituting a very important characteristic value can be measured with precision, but also the physical properties of the test material can be grasped with greater precision. The hardness data and the temperature data of the test material can be synchronously measured by providing a hardness sensor and a temperature sensor on the fixed support part of the tester body. The hardness tester according to the invention has a further advantage in that the digital signal output can be recorded or subjected to data processing. In addition, it is convenient for use since it can be produced in a small and handy unit.

What is claimed is:

1. A method for measuring the hardness of a test material, such as rubber, plastics, etc. comprising the steps of:
    detecting the amount of displacement of a feeler of a hardness tester,
    converting the amount of displacement into electric digital signals,
    evaluating the electric digital signals in terms of the hardness of the test material,
    detecting the maximum value, the intermediate value, and the stabilized value of the hardness of the test material from the evaluated electric digital signals,
    measuring the variation of hardness from the maximum value to the stabilized value after the lapse of a preset space of time, and
    displaying the hardness data of the test material on a display unit.

2. A hardness tester comprising:
    a feeler connected at one end of the hardness tester,
    a hardness sensor means, connected to the feeler, for detecting the amount of displacement of the feeler in terms of a variation of voltage,
    an evaluation means, connected to the hardness sensor, for converting said variation of voltage into a digital signal for hardness,
    a maximum value detecting circuit connected with said evaluation means,
    a timer connected to the evaluation means,
    a time presetting switch part connected to the timer, and
    a means, provided in front of the hardness tester, for digitally displaying the maximum value, the stabilized value, the intermediate value, and the difference value for the variation of the hardness from the maximum value to the stabilized value after the lapse of a preset space of time.

3. A hardness tester comprising:
    a tester body having an undersurface,
    a fixed support means for contacting a test material, said support means being formed on the undersurface of the tester body, a hardness sensor, being incorporated in the interior of the tester body, for obtaining hardness data of the test material, a feeler being provided on said fixed support means, a temperature sensor, being provided adjacent to the feeler, for obtaining temperature data of the test material, evaluation means, connected to the hardness sensor and the temperature sensor, for synchronously evaluating hardness data of the test material and temperature data of said test material, respectively, while the test material is being subjected to a hardness test, and means, connected to the evaluation means, for synchronously displaying the hardness data and the temperature data of the test material.

* * * * *